US011168057B2

(12) United States Patent
Kallem et al.

(10) Patent No.: US 11,168,057 B2
(45) Date of Patent: Nov. 9, 2021

(54) POLYMORPHS AND CO-CRYSTALS OF ROXADUSTAT

(71) Applicant: DR. REDDY'S LABORATORIES LIMITED, Hyderabad (IN)

(72) Inventors: Divya Jyothi Kallem, Hyderabad (IN); Rajesh Thipparaboina, Mancherial (IN); Deepika Pathivada, Vijayanagaram (IN); Vishweshwar Peddy, Hyderabad (IN); Shanmukha Prasad Gopi, Visakhapatnam (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/637,452

(22) PCT Filed: Aug. 10, 2018

(86) PCT No.: PCT/IB2018/056027
§ 371 (c)(1),
(2) Date: Feb. 7, 2020

(87) PCT Pub. No.: WO2019/030711
PCT Pub. Date: Feb. 14, 2019

(65) Prior Publication Data
US 2020/0247753 A1    Aug. 6, 2020

(30) Foreign Application Priority Data

Aug. 11, 2017  (IN) .............................. 201741028591
Nov. 8, 2017   (IN) .............................. 201741039745
Dec. 19, 2017  (IN) .............................. 201741045658
Jan. 11, 2018  (IN) .............................. 201841001251
Mar. 16, 2018  (IN) .............................. 201841009737

(51) Int. Cl.
*C07D 217/26*   (2006.01)
*C07C 275/02*   (2006.01)
*C07D 207/16*   (2006.01)
*C07D 213/82*   (2006.01)

(52) U.S. Cl.
CPC .......... *C07D 217/26* (2013.01); *C07C 275/02* (2013.01); *C07D 207/16* (2013.01); *C07D 213/82* (2013.01); *C07B 2200/13* (2013.01)

(58) Field of Classification Search
CPC ................................................ C07D 217/26
See application file for complete search history.

(56) References Cited

U.S. PATENT DOCUMENTS 7,323,475 B2   1/2008   Arend et al.
8,883,823 B2   11/2014  Witschi et al.
9,206,134 B2   12/2015  Kang et al.

FOREIGN PATENT DOCUMENTS

WO    2014014835 A2    1/2014

OTHER PUBLICATIONS

International Search Report dated Nov. 22, 2018, for corresponding International Patent Application No. PCT/IB2018/056027.
Written Opinion dated Nov. 22, 2018, for corresponding International Patent Application No. PCT/IB2018/056027.
Anaëlle Tilborg, et al; Pharmaceutical salts and cocrystals involving amino acids: A brief structural overview of the state-of-art, European Journal of Medicinal Chemistry 74 (2014).

*Primary Examiner* — Patricia L Morris
(74) *Attorney, Agent, or Firm* — Pergament & Cepeda LLP; Milagros A. Cepeda; Edward D. Pergament (57) ABSTRACT

The present invention provides crystalline Roxadustat Form-γ, crystalline Roxadustat Form-δ, process for the preparation of crystalline Roxadustat Form-γ, crystalline Roxadustat Form-δ and its pharmaceutical compositions thereof. The present invention also provides co-crystals of Roxadustat Form RLP, Roxadustat Form RNM and Roxadustat Form RU, process for their preparation and pharmaceutical composition thereof.

4 Claims, 4 Drawing Sheets

POLYMORPHS AND CO-CRYSTALS OF ROXADUSTAT

This application is a National Stage Application under 35 U.S.C. § 371 of PCT International Application No. PCT/162018/056027, filed Aug. 10, 2018, which takes priority from Indian Provisional Application Numbers IN 201741028591, filed Aug. 11, 2017, IN 201741039745, filed Nov. 8, 2017, IN 201741045658, filed Dec. 19, 2017, IN 201841001251, filed Jan. 11, 2018, IN 201841009737, filed Mar. 16, 2018, all of which are herein incorporated by reference in their entireties.

FIELD OF THE INVENTION

The present invention provides crystalline forms, solvates and co-crystals of Roxadustat, process for their preparation and pharmaceutical compositions thereof.

BACKGROUND OF THE INVENTION

Roxadustat (I) or FG-4592 is chemically known as [(4-Hydroxy-1-methyl-7-phenoxy-iso quinoline-3-carbonyl)-amino]-acetic acid. It is an oral small molecule inhibitor of HIF prolyl hydroxylases, or HIF-PHs, in Phase 3 clinical development for treating and preventing disorders associated with HIF, including anemia in chronic kidney disease, or CKD, ischemia, and hypoxia.

(I)

The U.S. Pat. No. 7,323,475 B2, Example D-81 (e), by referring Example D-78 (d), discloses a process for isolation of roxadustat by concentration of organic phases (EtOAc/Methanol) under vacuum.

The U.S. Pat. No. 8,883,823 B2 discloses crystalline Forms of roxadustat and their processes for the preparation. The crystalline forms are designated as Form A, Form B (hemihydrate), Form C (hexafluropropan-2-ol solvate) and Form D (DMSO: Water solvate). It further discloses various salts of roxadustat and amorphous roxadustat.

The U.S. Pat. No. 9,206,134 B2 discloses various crystalline Forms of roxadustat and their processes for the preparation. The crystalline forms are designated as Form I, Form II, Form III, Form IV, Form V, Form VI and Form VII.

The occurrence of different polymorphs is possible for some compounds. A single compound may give rise to a variety of solid forms having distinct physical properties. This variation in solid forms may be significant and may result in differences in pharmaceutical products with respect to solubility, bioavailability, stability and other properties. Because polymorphic forms can vary in their physical properties, regulatory authorities require that efforts shall be made to identify all the polymorphic forms, e.g., crystalline, solvated, etc., of new drug substances.

The existence and possible number of polymorphic forms for a given compound cannot be predicted, and there are no "standard" procedures that can be used to prepare polymorphic forms of a substance. However, new forms of a pharmaceutically useful compound may provide an opportunity to improve the performance characteristics of pharmaceutical products. For example, in some cases, different forms of the same drug can exhibit very different solubility and dissolution rates. The discovery of new polymorphic forms enlarges selection of materials with which formulation scientists can design a pharmaceutically acceptable dosage form of a drug with a targeted release profile or other desired characteristics. Therefore, there remains a need for preparing new and stable polymorphic forms of Roxadustat.

SUMMARY OF THE INVENTION

In a first embodiment of the present invention provides a crystalline Roxadustat Form-γ characterized by a PXRD comprising the peaks at about 6.56, 7.87, 9.22, 13.15, 18.22, 19.80, 20.94, 25.20 and 29.54±0.2° 2θ. In an embodiment, the invention provides a crystalline Roxadustat Form-γ, characterized by a PXRD having additional peaks at about 13.95 and 22.85±0.2° 2θ.

In a second embodiment of the present invention provides a process for preparation of crystalline Roxadustat Form-γ, comprising;
 a) dissolving roxadustat in formic acid;
 b) optionally, heating the solution of step a);
 c) isolating the crystalline Roxadustat Form-γ;
 d) optionally, drying the product at suitable temperature.

In a third embodiment of the present invention provides a process for preparation of crystalline Roxadustat Form-γ, comprising;
 a) dissolving roxadustat in formic acid;
 b) optionally, heating the solution of step a);
 c) adding anti-solvent to the solution of Roxadustat; or adding solution of Roxadustat to anti-solvent;
 d) isolating the crystalline Roxadustat Form-γ;
 e) optionally, drying the product at suitable temperature.

In a fourth embodiment of the present invention provides a crystalline Roxadustat Form-δ, characterized by a PXRD comprising the peaks at about 6.57, 9.21, 18.10, 19.67, 20.86, 25.10 and 29.47±0.2° 2θ. In an embodiment, the invention provides a crystalline Roxadustat Form-δ, characterized by a PXRD having additional peaks at about 13.02, 13.84 and 22.78±0.2° 2θ.

In a fifth embodiment of the present invention provides a process for preparation of crystalline Roxadustat Form-δ, comprising;
 a) slurrying crystalline Roxadustat form-γ in water;
 b) optionally, heating the solution of step a);
 c) isolating the crystalline Roxadustat Form-δ;
 d) optionally, drying the product at suitable temperature.

In a sixth embodiment, the present invention provides a co-crystal of Roxadustat comprising; Roxadustat and proline.

In a seventh embodiment of the present invention provides a co-crystal of Roxadustat comprising Roxadustat and L-proline.

In an eighth embodiment of the present invention provides a co-crystal of Roxadustat comprising Roxadustat and L-proline, designated as a crystalline form RLP of Roxadustat, characterized by power X-ray diffraction pattern having peaks at about 3.57, 7.15, 10.17, 10.74, 17.94 and 21.29±0.2 2θ°. In an another aspect, the present invention provides crystalline form RLP of Roxadustat, characterized by a PXRD having peaks at about 9.54, 14.31, 19.17 and 25.22±0.2 2θ°.

In a ninth embodiment of the present invention provides a process for preparation of co-crystals of Roxadustat (crystalline form RLP), comprising;
 a) grinding or contacting in solution the Roxadustat with L-proline;
 b) optionally, heating the mixture of step a);
 c) isolating co-crystals of Roxadustat (Crystalline form RLP).

In a tenth embodiment of the present invention provides a process for preparation of co-crystals of Roxadustat (crystalline form RLP), comprising;
 a) providing/dissolving L-proline solution with Roxadustat;
 b) optionally, heating the mixture of step a);
 c) isolating co-crystals of Roxadustat (Crystalline form RLP).

In a eleventh embodiment of the present invention provides a process for preparation of co-crystals of Roxadustat (crystalline form RLP) comprising the step of crystallizing Roxadustat and L-proline from solvent or solvent mixtures comprising water, methanol and acetone.

In a twelfth embodiment of the present invention provides a co-crystal of Roxadustat comprising; Roxadustat and Nicotinamide.

In a thirteenth embodiment of the present invention provides a co-crystal of Roxadustat comprising Roxadustat and Nicotinamide, designated as a crystalline form RNM of Roxadustat, characterized by power X-ray diffraction pattern having peaks at about 6.24, 10.84, 18.86, 22.20, 23.37, 26.41 and 29.24±0.2 2θ°.

In a fourteenth embodiment of the present invention provides a process for preparation of co-crystals of Roxadustat (crystalline form RNM), comprising;
 a) providing/dissolving nicotinamide solution with Roxadustat;
 b) optionally, heating the mixture of step a);
 c) isolating co-crystals of Roxadustat (Crystalline form RNM).

In a fifteenth embodiment of the present invention provides a co-crystal of Roxadustat comprising; Roxadustat and Urea.

In a sixteenth embodiment of the present invention provides a co-crystal of Roxadustat comprising Roxadustat and Urea, designated as a crystalline form RU of Roxadustat, characterized by power X-ray diffraction pattern having peaks at about 7.74, 14.79, 17.84, 18.39, 19.41, 20.89, 22.29, 23.22, 24.64 and 29.34±0.2 2θ°.

In a seventeenth embodiment of the present invention provides a process for preparation of co-crystals of Roxadustat (crystalline form RU), comprising;
 a) providing/dissolving urea solution with Roxadustat;
 b) optionally, heating the solution of step a);
 c) isolating co-crystals of Roxadustat (Crystalline form RU).

In a eighteenth embodiment of the present invention provides a pharmaceutical composition comprising crystalline forms of Roxadustat selected from the group comprising Form-γ, Form-δ, Form RLP, Form RNM and Form RU or mixtures thereof together with at least one pharmaceutically acceptable excipient.

DETAILED DESCRIPTION OF THE INVENTION

Based on a chemical structure, one cannot predict with any degree of certainty whether a compound will crystallize, under what conditions it will crystallize, how many crystalline solid forms of the compound might exist, or the solid-state structure of any of those forms.

The present invention results from the discovery of the solid forms of Roxadustat. The present invention also provides novel co-crystals of Roxadustat.

Definitions

The following definitions are used in connection with the present invention unless the context indicates otherwise.

"Hydrate" refers to a complex formed by the combining of Roxadustat and water. The term includes stoichiometric as well as non-stoichiometric hydrates.

"Solvate" refers to a complex formed by the combining of Roxadustat and a solvent.

"Co-crystal" as used herein is defined as a crystalline material comprising two or more compounds of which at least two are held together, wherein at least one of the compounds is a co-crystal former. "Co-crystal-former" as used herein is defined as a component with which Roxadustat is able to form co-crystals. The co-crystal former is part of the crystal lattice.

The terms "about," "general, "generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

The term "crystalline form" indicates that the Roxadustat is present in substantially crystalline Form. "Substantially" crystalline denotes that at least 80%, preferably 90% or 95%, more preferably all of the Roxadustat is crystalline form. In other words, "crystalline form" of Roxadustat denotes Roxadustat, which does not contain substantial amounts, preferably does not contain noticeable amounts, of any other crystalline portions of Roxadustat e.g. measurable upon X-ray powder diffraction analysis.

The term "optional" or "optionally" is taken to mean that the event or circumstance described in the specification may or may not occur, and that the description includes instances where the event occurs and instances where it does not.

In a first embodiment of the present invention provides a crystalline Roxadustat Form-γ characterized by a PXRD comprising the peaks at about 6.56, 7.87, 9.22, 13.15, 18.22, 19.80, 20.94, 25.20 and 29.54±0.2° 2θ. In an embodiment, the invention provides a crystalline Roxadustat Form-γ, characterized by a PXRD having additional peaks at about 13.95 and 22.85±0.2° 2θ.

Figure 1:
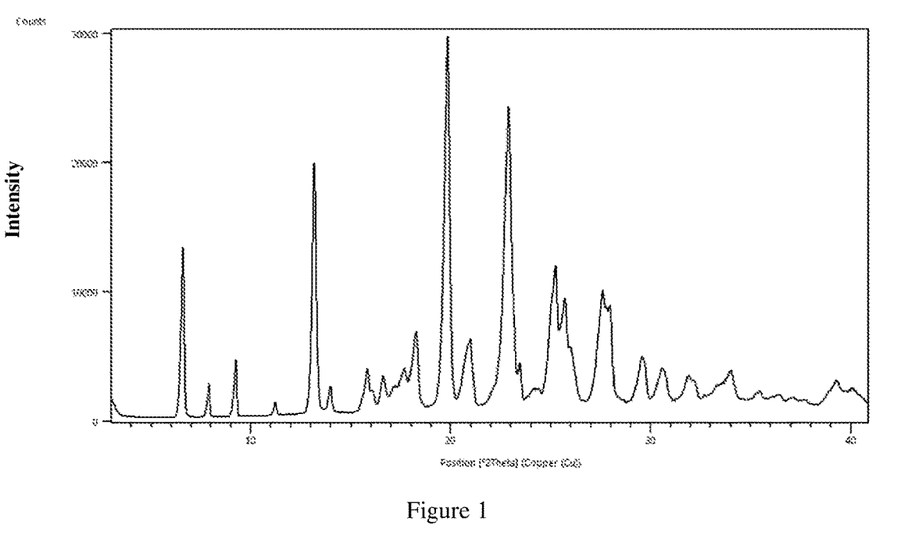
FIG. 1 illustrates the powder X-ray diffraction ("PXRD") pattern of crystalline Roxadustat Form-γ obtained from example-1.

In an embodiment, the present invention provides crystalline Roxadustat Form-γ, characterized by a PXRD substantially as shown in FIG. 1.

Figure 2:
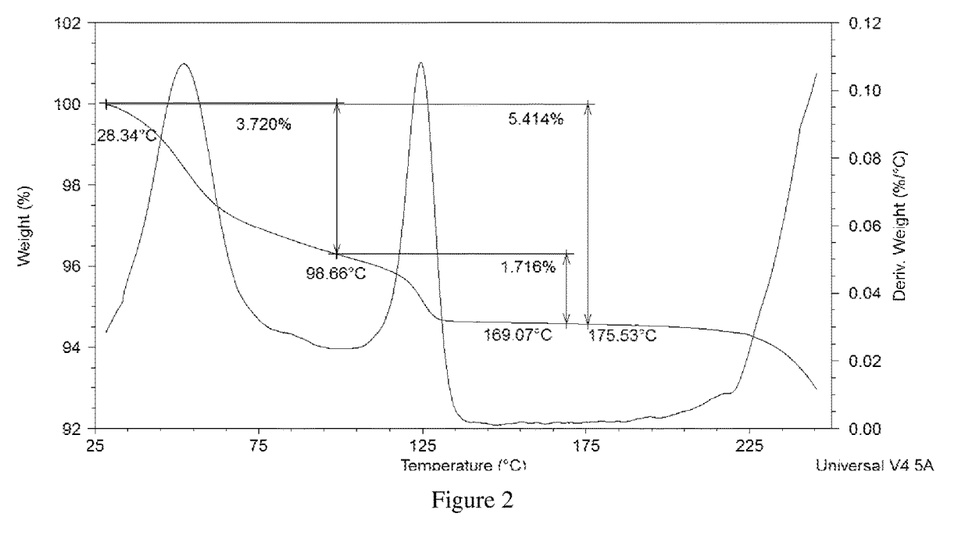
FIG. 2 illustrates thermogravimetic analysis (TGA) of crystalline Roxadustat Form-γ obtained from example-1.

In an embodiment, the present invention provides crystalline Roxadustat Form-γ characterized by TGA as shown in FIG. 2.

In a second embodiment of the present invention provides a process for preparation of crystalline Roxadustat Form-γ, comprising;
 a) dissolving roxadustat in formic acid;
 b) optionally, heating the solution of step a);
 c) isolating the crystalline Roxadustat Form-γ;
 d) optionally, drying the product at suitable temperature.

In embodiments of step a) involves the solution may optionally be treated with carbon, flux-calcined diatomaceous earth (Hyflow), or any other suitable material to remove color and/or to clarify the solution. In step a), dissolving the roxadustat in the solvent comprising formic acid.

The dissolution temperatures may range from about 0° C. to about the reflux temperature of the formic acid, or less than about 120° C., less than about 110° C., less than about 100° C., less than about 70° C., less than about 40° C., less than about 20° C., less than about 0° C., or any other suitable temperatures, as long as a clear solution of roxadustat is obtained without affecting its quality.

Optionally, the solution obtained above may be filtered to remove any insoluble particles. The insoluble particles may be removed suitably by filtration, centrifugation, decantation, or any other suitable techniques. The solution may be filtered by passing thorough paper, glass fiber, or other membrane material, or a bed of a clarifying agent such as celite or hyflow. Depending upon the equipment used and the concentration and temperature of the solution, the filtration apparatus may need to be preheated to avoid premature crystallization.

Step c) involves the isolation of crystalline roxadustat Form-γ can be effected, if desired, by any suitable methods including cooling, rapid cooling, concentrating the mass, adding an anti-solvent, adding seed crystals to induce crystallization or the like. Stirring or other alternate methods such as shaking, agitation, or the like, may also be employed for the isolation.

Suitable temperatures for isolation may be less than about 100° C., less than about 80° C., less than about 60° C., less than about 40° C., less than about 20° C., less than about 10° C., less than about 5° C., less than about 0° C., less than about −10° C., less than about −20° C., or any other suitable temperatures.

The isolated crystalline roxadustat Form-γ may be recovered by methods including decantation, centrifugation, gravity filtration, suction filtration, or any other technique for the recovery of solids under pressure or under reduced pressure. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

In a third embodiment of the present invention provides a process for preparation of crystalline Roxadustat Form-γ, comprising;
 a) dissolving roxadustat in formic acid;
 b) optionally, heating the solution of step a);
 c) adding anti-solvent to the solution of Roxadustat; or adding solution of
 Roxadustat to anti-solvent;
 d) isolating the crystalline Roxadustat Form-γ;
 e) optionally, drying the product at suitable temperature.

In embodiments of step a) involves the solution may optionally be treated with carbon, flux-calcined diatomaceous earth (Hyflow), or any other suitable material to remove color and/or to clarify the solution. In step a), dissolving the roxadustat in the solvent comprising formic acid.

Optionally, the solution obtained above may be filtered to remove any insoluble particles. The insoluble particles may be removed suitably by filtration, centrifugation, decantation, or any other suitable techniques. The solution may be filtered by passing thorough paper, glass fiber, or other membrane material, or a bed of a clarifying agent such as celite or hyflow. Depending upon the equipment used and the concentration and temperature of the solution, the filtration apparatus may need to be preheated to avoid premature crystallization.

The dissolution temperatures may range from about 0° C. to about the reflux temperature of the formic acid, or less than about 120° C., less than about 110° C., less than about 100° C., less than about 70° C., less than about 40° C., less than about 20° C., less than about 0° C., or any other suitable temperatures, as long as a clear solution of roxadustat is obtained without affecting its quality.

In embodiments of step c) involves adding anti-solvent to the solution obtained in step b), or adding the solution obtained in step b) to the anti-solvent, wherein the solution is made in step b) with only formic acid. After adding anti-solvent, the reaction mass may be maintained from 15 minutes to 24 hours.

Suitable anti-solvent used in step c) include, but are not limited to: alkanes, such as n-pentane, n-heptane, n-hexane, n-heptane or the like, ethers, such as diethyl ether, methyl tertiary butyl ether, diisopropyl ether, petroleum ether or the like cyclohexane or mixtures thereof.

The isolation of step d) can be effected, if desired, by any suitable separation methods such as precipitation, filtration, centrifugation, extraction, acid-base treatment, by scraping, or by shaking the container conventional isolation and refining means such as concentration, concentration under reduced pressure or by a combination of these procedures.

Suitable temperatures for isolation may be less than about 100° C., less than about 80° C., less than about 60° C., less than about 40° C., less than about 20° C., less than about 10°

C., less than about 5° C., less than about 0° C., less than about −10° C., less than about −20° C., or any other suitable temperatures.

In a fourth embodiment of the present invention provides a crystalline Roxadustat Form-δ, characterized by a PXRD comprising the peaks at about 6.57, 9.21, 18.10, 19.67, 20.86, 25.10 and 29.47±0.2° 2θ. In an embodiment, the invention provides a crystalline Roxadustat Form-δ, characterized by a PXRD having additional peaks at about 13.02, 13.84 and 22.78±0.2° 2θ.

Figure 3:
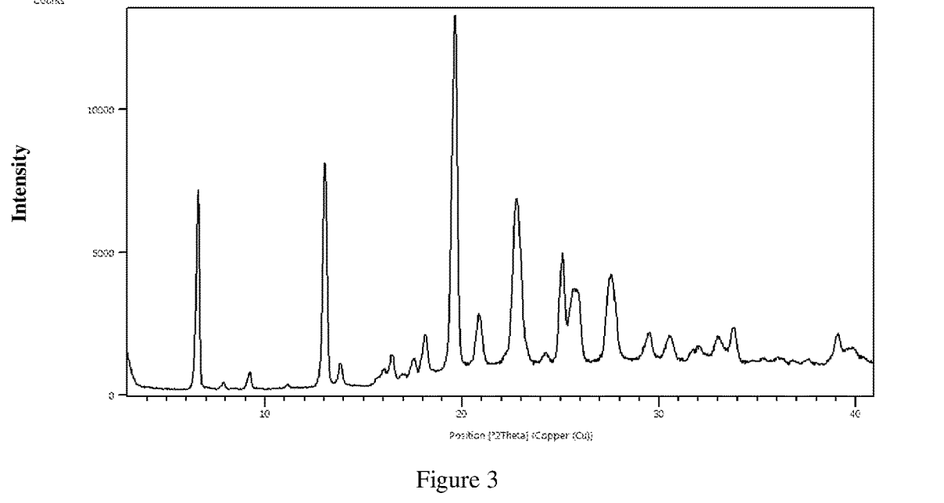
FIG. 3 illustrates the powder X-ray diffraction ("PXRD") pattern of crystalline Roxadustat Form-δ obtained from example-5.

In an embodiment, the present invention provides crystalline Roxadustat Form-δ, characterized by a PXRD substantially as shown in FIG. 3. A crystalline Roxadustat Form-δ, which is a hydrate.

Figure 4:
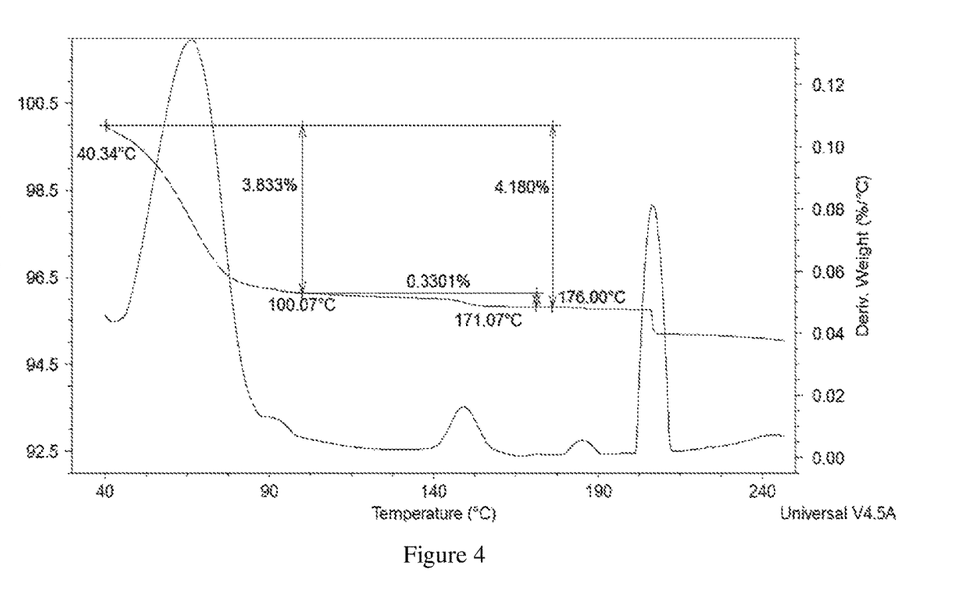
FIG. 4 illustrates thermogravimetic analysis (TGA) of crystalline Roxadustat Form-δ obtained from example-5.

In an embodiment, the present invention provides crystalline Roxadustat Form-δ, characterized by TGA as shown in FIG. 4.

In a fifth embodiment of the present invention provides a process for preparation of crystalline Roxadustat Form-δ, comprising;
 a) slurrying crystalline Roxadustat form-γ in water;
 b) optionally, heating the solution of step a);
 c) isolating the crystalline Roxadustat Form-δ;
 d) optionally, drying the product at suitable temperature.

In embodiments of step a) involves the solution may optionally be treated with carbon, flux-calcined diatomaceous earth (Hyflow), or any other suitable material to remove color and/or to clarify the solution. In step a), slurrying crystalline Roxadustat Form-γ in water.

Slurrying crystalline Roxadustat Form-γ in water may be less than for 24 hours, less than 20 hours, less than 16 hours, less than 12 hours, less than 8 hours, less than 4 hours.

Step c) involves the isolation of crystalline roxadustat Form-δ can be effected, if desired, by any suitable methods including cooling, rapid cooling, concentrating the mass, adding an anti-solvent, adding seed crystals to induce crystallization or the like. Stirring or other alternate methods such as shaking, agitation, or the like, may also be employed for the isolation.

Suitable temperatures for isolation may be less than about 100° C., less than about 80° C., less than about 60° C., less than about 40° C., less than about 20° C., less than about 10° C., less than about 5° C., less than about 0° C., less than about −10° C., less than about −20° C., or any other suitable temperatures.

The isolated crystalline Roxadustat Form-δ may be recovered by methods including decantation, centrifugation, gravity filtration, suction filtration, or any other technique for the recovery of solids under pressure or under reduced pressure. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

A cooling crystallization of Roxadustat from formic acid solvent resulted in Form-γ of Roxadustat. Form γ is a Formic acid and water mixed solvate, in which formic acid content vary from 2 to 3% and water content ranges between 4 to 5%. Form γ, when slurried in water resulted into Form-δ which is a hydrate of Roxadustat. Water content in Form δ ranges between 4.5 to 5.5% i.e., equivalent to monohydrate and formic acid content is <5000 ppm.

In a sixth embodiment, the present invention provides a co-crystal of Roxadustat comprising; Roxadustat and proline.

The term "co-crystal" as used herein means a crystalline material comprises two or more unique solids at room temperature, each containing distinctive physical characteristics, such as structure, melting point and heats of fusion. The co-crystals of the present invention comprise a co-crystal former (proline) hydrogen bonded to Roxadustat.

Roxadustat input material may be crystalline or amorphous form. Co-crystals herein can be anhydrous; can also exist as co-crystal hydrates or solvates thereof.

In a seventh embodiment of the present invention provides a co-crystal of Roxadustat comprising Roxadustat and L-proline.

In an eighth embodiment of the present invention provides a co-crystal of Roxadustat comprising Roxadustat and L-proline, designated as a crystalline form RLP of Roxadustat, characterized by power X-ray diffraction pattern having peaks at about 3.57, 7.15, 10.17, 10.74, 17.94 and 21.29±0.2 2θ°. In an another aspect, the present invention provides crystalline form RLP of Roxadustat, characterized by a PXRD having peaks at about 9.54, 14.31, 19.17 and 25.22±0.2 2θ°.

Figure 5:
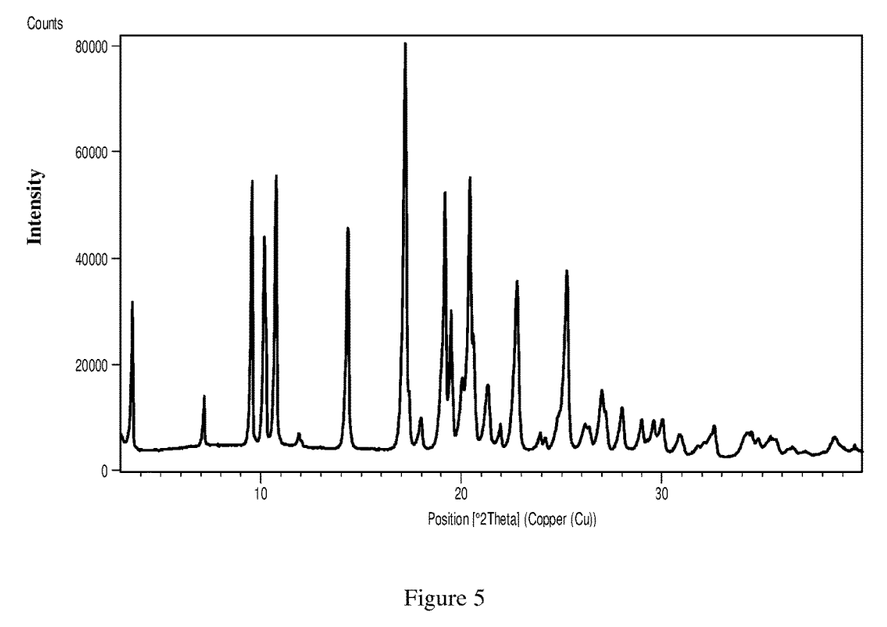
FIG. 5 illustrates the powder X-ray diffraction ("PXRD") pattern of co-crystal of Roxadustat with L-proline prepared by the method of example-9

In an embodiment, the present invention provides crystalline form RLP of Roxadustat, characterized by a PXRD substantially as shown in FIG. 5.

In a ninth embodiment of the present invention provides a process for preparation of co-crystal of Roxadustat (crystalline form RLP), comprising;
 a) grinding or contacting in solution the Roxadustat with L-proline;
 b) optionally, heating the mixture of step a);
 c) isolating co-crystals of Roxadustat (Crystalline form RLP).

The grinding process comprises dry grinding or wet grinding of Roxadustat with L-proline. In dry grinding process, Roxadustat and L-proline are ground in a mortar, a grinder or a mill to obtain a co-crystal. Grinding in a mortar involves physical grinding of Roxadustat and co-crystal. In wet grinding process, Roxadustat and L-proline are ground in mortar, a grinder or a mill with the solvent or mixture of solvents followed by drying to obtain the co-crystal. The solvent for wet grinding process includes but are not limited to: water, alcohol solvents, such as, for example, methanol, ethanol, isopropanol or the like; ketone solvents such as acetone, methyl ethyl ketone, diethyl ketone, methyl isopropyl ketone, methyl isobutyl ketone or the like; polar aprotic solvents such as dimethyl formamide, dimethyl sulfoxide, dimethyl acetamide, N-methyl pyrrolidone or the like; ethers which includes tetrahydrofuran, 1,4-dioxane or the like; halogenated hydrocarbon which includes dichloromethane, trichloromethane or the like;

The amount of solvent used for wet grinding is in the range of up to about 10% by weight (w/w) of solid components. For example, a weight percent of less than or equal to about 0.1, 0.2, 0.3, 0.4, 0.5, 0.6, 0.7, 0.8, 0.9, 1, 2, 3, 4, 5, 6, 7, 8, and 9 may be used.

Co-crystal may be formed by contacting the Roxadustat with L-proline in solution. The process comprises a) dissolving Roxadustat and L-proline in a suitable solvent; b) cooling the solution and c) isolation of the co-crystal formed.

In the process according to the invention, contacting Roxadustat with L-proline involves either solubilizing Roxadustat and adding L-proline, or solubilizing L-proline and adding Roxadustat to it.

Suitable solvents which can be used for preparing the solution include but are not limited to water, alcohol solvents, such as, for example, methanol, ethanol, isopropanol or the like; ketone solvents such as acetone, methyl ethyl ketone, diethyl ketone, methyl isopropyl ketone, methyl isobutyl ketone or the like; polar aprotic solvents such as acetonitrile, dimethyl formamide, dimethyl sulfoxide, dimethyl acetamide, N-methyl pyrrolidone or the like; ethers which includes tetrahydrofuran, 1,4-dioxane or the like; halogenated hydrocarbon which includes dichloromethane, trichloromethane or the like;

The dissolution temperatures can range from about 20 to 120° C. depending on the solvent used for dissolution. Any other temperature is also acceptable as long as a clear solution is obtained.

For isolation to occur, the reaction mass may be maintained further at temperatures lower than the dissolution temperatures such as for example below about 10° C. to about 25° C., for a period of time as required for a more complete isolation of the product. The exact cooling temperature and time required for complete crystallization can be readily determined by a person skilled in the art and will also depend on parameters such as concentration and temperature of the solution or slurry.

Optionally, isolation may be initiated or enhanced by methods such as cooling, seeding, partial removal of the solvent from the solution, using anti-solvent or a combination thereof.

The method by which the solid material is recovered from the final mixture, with or without cooling below the operating temperature, can be any of techniques such as filtration by gravity or by suction, decantation, centrifugation, and the like.

Optionally, the obtained product is further dried. Drying can be carried out at reduced pressures. Drying can be suitably carried out in a tray dryer, vacuum oven, air oven, or using a fluidized bed drier, agitated thin dryer, spin flash dryer, flash dryer or the like.

In a tenth embodiment of the present invention provides a process for preparation of co-crystals of Roxadustat (crystalline form RLP), comprising;

a) providing/dissolving L-proline solution with Roxadustat;
b) optionally, heating the solution of step a);
c) isolating co-crystals of Roxadustat (Crystalline form RLP).

Suitable solvent that may be used in step (a) include, but are not limited to water, alcohol solvents, such as, for example, methanol, ethanol, isopropanol or the like; ketone solvents such as acetone, methyl ethyl ketone, diethyl ketone, methyl isopropyl ketone, methyl isobutyl ketone or the like; ether solvents, such as, for example, diethyl ether, diisopropyl ether, tert-butyl methyl ether, dibutyl ether, tetrahydrofuran, 1,2-dimethoxyethane, 2-methoxyethanol, 2-ethoxy ethanol, anisole, 1,4-dioxane, or the like; aromatic hydrocarbon solvents, such as, for example, toluene, xylene, chlorobenzene, tetralin, or the like; chlorinated hydrocarbon solvents, such as chloroform, dichloromethane or mixtures thereof.

Optionally, the solution obtained above may be filtered to remove any insoluble particles. The insoluble particles may be removed suitably by filtration, centrifugation, decantation, or any other suitable techniques. The solution may be filtered by passing through paper, glass fiber, or other membrane material, or a bed of a clarifying agent such as celite or hyflow. Depending upon the equipment used the concentration and temperature of the solution, the filtration apparatus may need to be preheated to avoid premature crystallization.

The temperature at which the above steps may be carried out in between about 20° C. and about 100° C., preferably at about 25° C. and about 50° C.

In a eleventh embodiment of the present invention provides a process for preparation of co-crystals of Roxadustat (crystalline form RLP) comprising the step of crystallizing Roxadustat and L-Proline from solvent or solvent mixtures comprising water, methanol and acetone.

Figure 6:
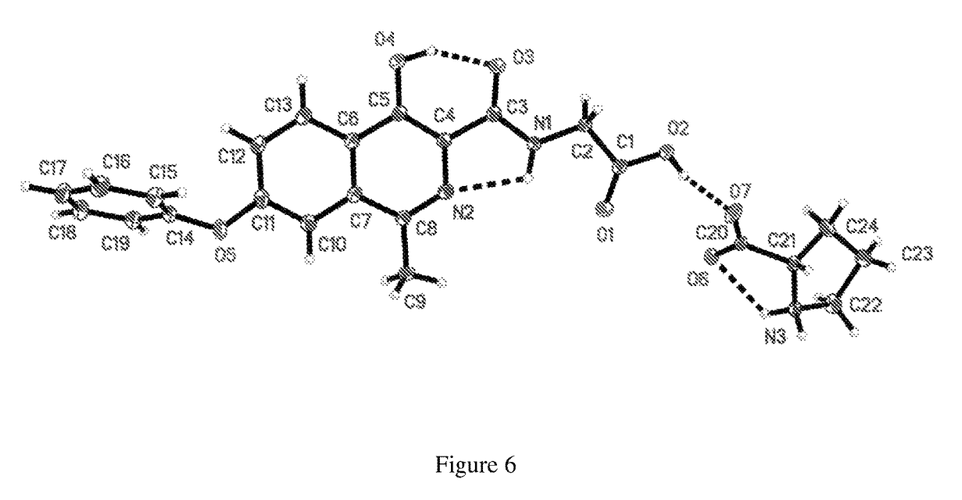
FIG. 6 illustrates ORTEP of Roxadustat●L-proline (1:1) Co-crystal (Form-RLP) Displacement ellipsoids are drawn at the 50% probability level and H atoms are shown as small spheres of arbitrary radii. Dashed line indicates hydrogen bonds.

In an embodiment of the present invention provides an ORTEP diagram of Roxadustat●L-Proline (1:1) co-crystal as shown in FIG. 6. Displacement ellipsoids are drawn at the 50% probability level and H atoms are shown as small spheres of arbitrary radii. Dashed line indicates hydrogen bonds.

Roxadustat●L-Proline Co-Crystal (Crystalline Form RLP):

Co-crystal of Roxadustat and L-proline crystallizes from acetone, methanol and water in the monoclinic space group $P2_1$. The asymmetric unit consists of one molecule of Roxadustat and one molecule of L-proline. Cocrystal involves an O—H (carboxy) . . . O (carboxylate) hydrogen bond between the carboxylic acid group of the Roxadustat and carboxylate of proline. The hydroxyl group of Roxadustat is involved in an intramolecular O—H (hydroxy) . . . O (carboxy) hydrogen bond with the carboxy group.

TABLE 1

Crystal data and structure refinement for Roxadustat●L-Proline (1:1) Co-crystal:

| | |
|---|---|
| Empirical formula | $(C_{19}H_{16}N_2O_5)(C_5H_9NO_2)$ |
| Formula weight | 467.47 |
| Temperature | 100(2) K. |
| Wavelength | 0.71073 Å |
| Crystal system | Monoclinic |
| Space group | $P2_1$ |
| Unit cell dimensions | a = 9.117(14) Å |
| | b = 4.940(8) Å |
| | c = 24.644(4) Å |
| | α = 90 |
| | β = 90.37(4)° |
| | γ = 90° |
| Volume | 1110.1(3) Å$^3$ |
| Z | 2 |
| Density (calculated) | 1.399 mg/m$^3$ |
| Absorption coefficient | 0.104 mm$^{-1}$ |
| F(000) | 492 |
| Crystal size | 0.220 × 0.130 × 0.090 mm$^3$ |
| θ range for data collection | 2.234 to 30.613° |
| Index ranges | −13 <= h <= 13, −7 <= k <=7, −35 <= l <= 33 |
| Reflections collected | 19162 |
| Independent reflections | 6761 [R(int) = 0.0235] |
| Refinement method | Full-matrix least-squares on F$^2$ |
| Data/restraints/parameters | 6761/1/338 |
| Goodness-of-fit on F$^2$ | 1.040 |
| Final R indices [I > 2σ(I)] | R1 = 0.0366, wR2 = 0.0883 |
| R indices (all data) | R1 = 0.0412, wR2 = 0.0909 |

TABLE 1-continued

Crystal data and structure refinement for Roxadustat•L-Proline (1:1) Co-crystal:

| | |
|---|---|
| Largest diff. peak and hole | 0.297 and −0.245 e · Å$^{-3}$ |
| Measurement | Bruker D8 QUEST PHOTON-100 Detector |
| Software Used | SHELXTL-PLUS |

TABLE 2

Hydrogen bonds of Roxadustat? L-Proline (1:1) Co-crystal (Form-RLP):

| D-H . . . A | D-H, Å | d (H . . . A), Å | D (D . . . A), Å | DHA (θ, °) |
|---|---|---|---|---|
| $N_1$—H . . . $N_2$ | 0.93(3) | 2.21(2) | 2.656(2) | 108.7(19) |
| $N_3$—H . . . $O_6$ | 0.92(3) | 1.92(3) | 2.762(2) | 152(2) |
| $O_4$—H . . . $O_3$ | 0.92(3) | 1.80(3) | 2.6293(17) | 150(2) |
| $O_2$—H . . . $O_7$ | 0.82(3) | 1.70(3) | 2.5008(18) | 162(3) |

Roxadustat L-Proline co-crystal (Crystalline form RLP) were found to be stable in all three ICH conditions for three months. The data presented below substantiate that the Form RLP has a high storage stability.

Pack-1 (Normal LDPE Bag with 1 g Silica Gel, Packed in a HDPE Container):

| Duration | Storage conditions | Water content (% w/w) | Purity (%) | PXRD |
|---|---|---|---|---|
| Initial | 40 ± 2° C.; | 0.09 | 99.84 | Form RLP |
| 1$^{st}$ Month | 75 ± 5% RH | 0.16 | 99.84 | No change |
| 3$^{rd}$ Month | | 0.21 | 99.83 | No change |
| Initial | 25 ± 2° C.; | 0.09 | 99.84 | Form RLP |
| 1st Month | 60 ± 5% RH | 0.14 | 99.84 | No change |
| 3rd Month | | 0.12 | 99.86 | No change |
| Initial | 2-8° C. | 0.09 | 99.84 | Form RLP |
| 1st Month | | 0.11 | 99.84 | No change |
| 3rd Month | | 0.14 | 99.85 | No change |

Pack-2 (Black Colored LDPE Bag with 1 g Silica Gel, Packed in a HDPE Container):

| Duration | Storage conditions | Water content (% w/w) | Purity (%) | PXRD |
|---|---|---|---|---|
| Initial | 40 ± 2° C.; | 0.09 | 99.84 | Form RLP |
| 1$^{st}$ Month | 75 ± 5% RH | 0.14 | 99.83 | No change |
| 3$^{rd}$ Month | | 0.11 | 99.85 | No change |
| Initial | 25 ± 2° C.; | 0.09 | 99.84 | Form RLP |
| 1st Month | 60 ± 5% RH | 0.11 | 99.84 | No change |
| 3rd Month | | 0.13 | 99.82 | No change |
| Initial | 2-8° C. | 0.09 | 99.84 | Form RLP |
| 1st Month | | 0.14 | 99.82 | No change |
| 3rd Month | | 0.16 | 99.85 | No change |

In a twelfth embodiment of the present invention provides a co-crystal of Roxadustat comprising; Roxadustat and Nicotinamide.

The term "co-crystal" as used herein means a crystalline material comprising two or more unique solids at room temperature, each containing distinctive physical characteristics, such as structure, melting point and heats of fusion. The co-crystals of the present invention comprise a co-crystal former (nicotinamide) hydrogen bonded to Roxadustat.

Roxadustat input material may be crystalline or amorphous form. Co-crystals herein can be anhydrous; can also exist as co-crystal hydrates or solvates thereof.

In a thirteenth embodiment of the present invention provides a co-crystal of Roxadustat comprising Roxadustat and Nicotinamide, designated as a crystalline form RNM of Roxadustat, characterized by power X-ray diffraction pattern having peaks at about 6.24, 10.84, 18.86, 22.20, 23.37, 26.41 and 29.24±0.2 2θ°.

Figure 7:
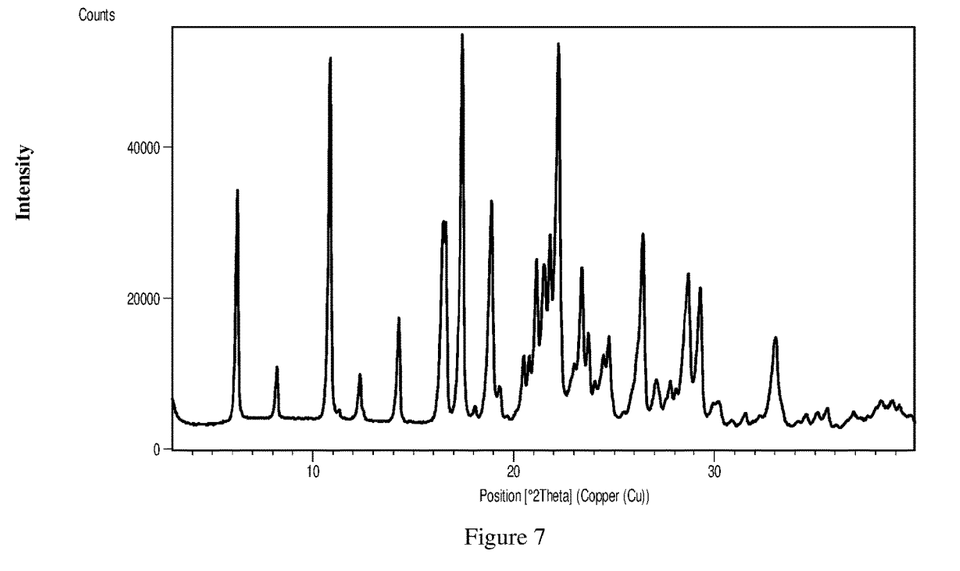
FIG. 7 illustrates the powder X-ray diffraction ("PXRD") pattern of co-crystal of Roxadustat with Nicotinamide prepared by the method of example-14.

In an embodiment, the present invention provides crystalline form RNM of Roxadustat, characterized by a PXRD substantially as shown in FIG. 7.

In a fourteenth embodiment of the present invention provides a process for preparation of co-crystals of Roxadustat (crystalline form RNM), comprising;
a) providing/dissolving nicotinamide solution with Roxadustat;
b) optionally, heating the solution of step a);
c) isolating co-crystals of Roxadustat (Crystalline form RNM).

Suitable solvent that may be used in step (a) include, but are not limited to water, alcohol solvents, such as, for example, methanol, ethanol, isopropanol or the like; ketone solvents such as acetone, methyl ethyl ketone, diethyl ketone, methyl isopropyl ketone, methyl isobutyl ketone or the like; ether solvents, such as, for example, diethyl ether, diisopropyl ether, tert-butyl methyl ether, dibutyl ether, tetrahydrofuran, 1,2-dimethoxyethane, 2-methoxyethanol, 2-ethoxy ethanol, anisole, 1,4-dioxane, or the like; aromatic hydrocarbon solvents, such as, for example, toluene, xylene, chlorobenzene, tetralin, or the like; chlorinated hydrocarbon solvents, such as chloroform, dichloromethane or mixtures thereof.

Optionally, the solution obtained above may be filtered to remove any insoluble particles. The insoluble particles may be removed suitably by filtration, centrifugation, decantation, or any other suitable techniques. The solution may be filtered by passing through paper, glass fiber, or other membrane material, or a bed of a clarifying agent such as celite or hyflow. Depending upon the equipment used the concentration and temperature of the solution, the filtration apparatus may need to be preheated to avoid premature crystallization.

The temperature at which the above steps may be carried out in between about 20° C. and about 100° C., preferably at about 25° C. and about 60° C.

The isolation of step c) can be effected, if desired, by any suitable separation methods such as precipitation, filtration, centrifugation, extraction, acid-base treatment, by scraping, or by shaking the container conventional isolation and refining means such as concentration, concentration under reduced pressure or by a combination of these procedures.

Roxadustat•nicotinamide co-crystal (Crystalline form RNM) was found to be stable in all three ICH conditions for three months. The data presented below substantiate that the Form RNM has a high storage stability.

Pack-1 (LDPE Bag with 1 g Molecular Sieve, Packed in a HDPE Container):

| Duration | Storage conditions | Water content (% w/w) | Purity (%) | PXRD |
|---|---|---|---|---|
| Initial | 40 ± 2° C.; | 0.12 | 99.57 | Form RNM |
| 1$^{st}$ Month | 75 ± 5% RH | 0.10 | 99.65 | No change |
| 3$^{rd}$ Month | | 0.07 | 99.62 | No change |

-continued

| Duration | Storage conditions | Water content (% w/w) | Purity (%) | PXRD |
|---|---|---|---|---|
| Initial | 25 ± 2° C.; | 0.12 | 99.57 | Form RNM |
| 1st Month | 60 ± 5% RH | 0.07 | 99.63 | No change |
| 3rd Month | | 0.08 | 99.64 | No change |
| Initial | 2-8° C. | 0.12 | 99.57 | Form RNM |
| 1st Month | | 0.08 | 99.66 | No change |
| 3rd Month | | 0.08 | 99.66 | No change |

Pack-2 (LDPE Bag with 1 g Silica Gel, Packed in a HDPE Container):

| Duration | Storage conditions | Water content (% w/w) | Purity (%) | PXRD |
|---|---|---|---|---|
| Initial | 40 ± 2° C.; | 0.12 | 99.57 | Form RNM |
| 1$^{st}$ Month | 75 ± 5% RH | 0.12 | 99.61 | No change |
| 3$^{rd}$ Month | | 0.07 | 99.62 | No change |
| Initial | 25 ± 2° C.; | 0.12 | 99.57 | Form RNM |
| 1st Month | 60 ± 5% RH | 0.07 | 99.65 | No change |
| 3rd Month | | 0.11 | 99.64 | No change |
| Initial | 2-8° C. | 0.12 | 99.57 | Form RNM |
| 1st Month | | 0.10 | 99.62 | No change |
| 3rd Month | | 0.08 | 99.65 | No change |

In a fifteenth embodiment of the present invention provides a co-crystal of Roxadustat comprising; Roxadustat and Urea.

In a sixteenth embodiment of the present invention provides a co-crystal of Roxadustat comprising Roxadustat and Urea, designated as a crystalline form RU of Roxadustat, characterized by power X-ray diffraction pattern having peaks at about 7.74, 14.79, 17.84, 18.39, 19.41, 20.89, 22.29, 23.22, 24.64 and 29.34±0.2 2θ°.

Figure 8:
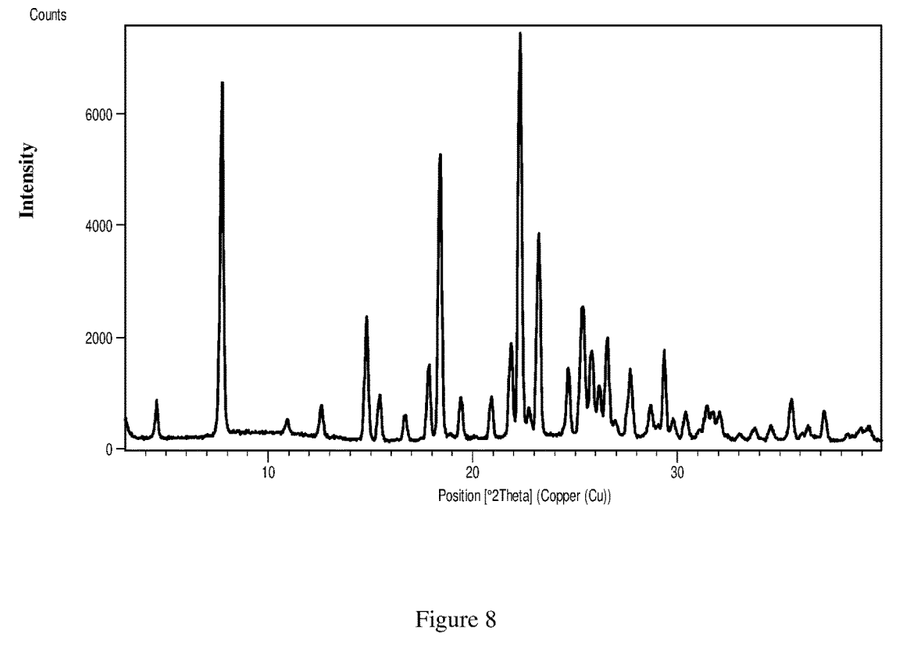
FIG. 8 illustrates the powder X-ray diffraction ("PXRD") pattern of co-crystal of Roxadustat with Urea prepared by the method of example-15.

In an embodiment, the present invention provides crystalline form RU of Roxadustat, characterized by a PXRD substantially as shown in FIG. 8.

In a seventeenth embodiment of the present invention provides a process for preparation of co-crystals of Roxadustat (crystalline form RU), comprising;
 a) providing/dissolving urea solution with Roxadustat;
 b) optionally, heating the solution of step a);
 c) isolating co-crystals of Roxadustat (Crystalline form RU).

The solvents and reaction conditions for steps (a) to (c) may be selected from one or more suitable solvents and process conditions as described in the steps of the fourteenth embodiment of the present invention.

Drying in the embodiments of the present invention may be suitably carried out by using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 30 minutes to about 24 hours, or longer.

All PXRD data reported herein are obtained using a PANalytical X-ray Diffractometer and Bruker D8 advance X-ray Diffractometer with copper Kα radiation.

Roxadustat that is used as starting material for the preparation of any of the solid forms of present application may be purified before using by employing any of the purification techniques known in the art such as recrystallization, slurrying or chromatography or according to the procedures described or exemplified in the instant application. Starting material may be either in a crystalline or amorphous state or an alternate crystalline form of Roxadustat known in the art.

In a eighteenth embodiment of the present invention provides a pharmaceutical composition comprising crystalline forms of Roxadustat selected from the group comprising Form-γ, Form-δ, Form RLP, Form RNM and Form RU or mixtures thereof together with at least one pharmaceutically acceptable excipient.

The pharmaceutical composition of the present invention may be formulated in accordance with conventional methods, and may be prepared in the form of oral formulations such as tablets, pills, powders, capsules, syrups, emulsions, micro emulsions, and others, or formulation for parenteral injection, e.g., intramuscular, intravenous, or subcutaneous administration.

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present application. While particular aspects of the present application have been illustrated and described, it would be obvious to those skilled in the art that various other changes and modifications can be made without departing from the spirit and scope of the invention. It is therefore intended to cover in the appended claims all such changes and modifications that are within the scope of this application.

EXAMPLES

Example-1: Preparation of Crystalline Roxadustat Form-γ

Roxadustat (3 g) was added to formic acid (30 mL) at room temperature. The reaction temperature was increased to 95° C. to obtain clear solution. The solution was filtered at room temperature for particle free. The filtrate was cooled rapidly to −5° C. and maintained for 120 minutes. The obtained solid was filtered and dried under vacuum at 50° C. for about 120 minutes to obtain the title compound.

HPLC formic acid content: 1.89%; Water content by KF: 4.48%

Example-2: Preparation of Crystalline Roxadustat Form-γ

Roxadustat (1 g) was added to formic acid (12 mL) at room temperature. The reaction temperature was increased to 95° C. to obtain clear solution. The solution was filtered at room temperature for particle free. The above filtrate solution was added to cyclohexane (50 mL) at 5° C. and maintained for about 120 minutes. The obtained compound was filtered and dried under vacuum at 50° C. for 60 minutes to obtain the title compound.

Example-3: Preparation of Crystalline Roxadustat Form-γ

Roxadustat (1 g) was added to formic acid (12 mL) at room temperature. The reaction temperature was increased to 95° C. to obtain clear solution. The solution was filtered at room temperature for particle free. The above filtrate solution was added to n-heptane (50 mL) at 5° C. and maintained for about 120 minutes. The obtained compound was filtered and dried under vacuum at 50° C. for 60 minutes to obtain the title compound.

Example-4: Preparation of Crystalline Roxadustat Form-γ

Roxadustat (7.5 g) was added to formic acid (50 mL) at room temperature. The reaction temperature was increased to 95° C. to obtain clear solution. The solution was filtered at room temperature for particle free. The above filtrate solution was added to n-heptane (150 mL) at −5° C. and maintained for about 120 minutes. The obtained compound was filtered and dried under vacuum at 50° C. for 60 minutes to obtain the title compound.

Example-5: Preparation of Crystalline Roxadustat Form-δ

Roxadustat Form-γ (500 mg) was added to water (4 mL) at room temperature and stirred for about 4 hours. Filtered the slurry obtained and dried under vacuum tray drier at 60° C. for about 120 minutes to obtain the title compound.
HPLC formic acid content: 0.49%; Water content by KF: 5.38%

Example-6: Preparation of Crystalline Roxadustat Form-δ

Roxadustat Form-γ (100 mg) and water (4 mL) were charged in to a glass vial at 25° C. and stirred for 24 hours on a High Throughput Screening (HTS) platform. The solid was filtered and dried at 25° C. to obtain the title compound.

Example-7: Preparation of Co-Crystal of Roxadustat with L-Proline

Roxadustat (0.352 g) and L-proline (0.116 g) were taken in a mortar and ground using a pestle at room temperature for 10 minutes. To the powder obtained a mixture of methyl ethyl ketone (1 mL) and DMSO (0.2 mL) was added and ground for 30 minutes to obtain the slurry, followed by drying in Air Tray Drier at 60° C. for 60-90 minutes to obtain the title co-crystal.

Example-8: Preparation of Co-Crystal of Roxadustat with L-Proline

Roxadustat (0.704 g) and L-proline (0.232 g) were taken in a mortar and ground using a pestle at room temperature for 10 minutes. Acetone (2×2 mL) was added to the above mixture and ground for 30 (15×2) minutes to obtain the mixture, followed by drying in Air Tray Drier at 60° C. for 120 minutes. The resultant powder and acetone (4 mL) were taken into a glass vial at room temperature. The mixture was slurried for 3-4 hours. Filtered the suspension under vacuum at room temperature to obtain the title co-crystal.

Example-9: Preparation of Co-Crystal of Roxadustat with L-Proline

Water (40 m L) was dispensed into a crystallization vessel at room temperature and it was heated to 40° C. L-proline (3.27 g) was added to hot water. To the above mixture methanol (40 mL) was added at 40° C. Acetone (400 mL) was added to the resultant solution at 42° C. Roxadustat (10 g) was added to the resultant solution at 45° C. and stirred for 20-30 minutes. The reaction mixture was cooled to 5° C. at 1° C./min and maintained for 1-2 hours. The obtained material was filtered under vacuum, de-lumped and dried in Vacuum Tray Dryer (VTD) at 45° C. for 4-5 hours to obtain the title co-crystal.

Example-10: Preparation of Co-Crystal of Roxadustat with L-Proline

Water (40 mL) was dispensed into a crystallization vessel at room temperature and it was heated to 40° C. L-proline (4.32 g) was added to hot water. To the above mixture methanol (40 mL) was added at 40° C. Acetone (400 mL) was added to the resultant solution at 42° C. Roxadustat (13.2 g) was added to the resultant solution at 45° C. and stirred for 20-30 minutes. The reaction mixture was cooled to 5° C. at 1° C./min and maintained for 1-2 hours. The obtained material was filtered under vacuum, de-lumped and dried in Vacuum Tray Dryer (VTD) at 50° C. for 3-4 hours to obtain the title co-crystal. Yield: 57%

Example-11: Preparation of Co-Crystal of Roxadustat with Nicotinamide

Methanol (4 mL) was dispensed into a crystallization vessel at room temperature and it was heated to 45° C. Nicotinamide (0.347 g) was added to hot methanol. To the above mixture acetone (40 mL) was added at 45° C. Roxadustat (1 g) was added to the resultant solution at 45° C. and stirred for 20-30 minutes. The resultant mixture was filtered under vacuum. Filtered solution was added to the other crystallization vessel at 45° C. The reaction mixture was cooled to 5° C. and stirred for 60 minutes. The reaction mixture was further cooled to −10° C. The obtained material was filtered and dried in Vacuum Tray Dryer (VTD) at 45° C. for 2-3 hours to obtain the title co-crystal.

Example-12: Preparation of Co-Crystal of Roxadustat with Nicotinamide

Methanol (2.5 mL) was dispensed into a crystallization vessel at room temperature and it was heated to 60° C. Nicotinamide (0.347 g) was added to hot methanol. To the above mixture methyl ethyl ketone (25 mL) was added at 60° C. Roxadustat (1 g) was added to the resultant solution at 60° C. and stirred for 20-30 minutes. The resultant mixture was filtered under vacuum. Filtered solution was added to the other crystallization vessel at 60° C. The reaction mixture was cooled to 5° C. and stirred for 60 minutes. The reaction mixture was further cooled to −10° C. and stirred for 2 hours. The obtained material was filtered and dried in vacuum Tray Dryer (VTD) at 45° C. for 2-3 hours to obtain the title co-crystal.

Example-13: Preparation of Co-Crystal of Roxadustat with Nicotinamide

Methanol (5.5 mL) was dispensed into a crystallization vessel at room temperature and it was heated to 60° C. Nicotinamide (0.694 g) was added to hot methanol. To the above mixture methyl ethyl ketone (55 mL) was added at 65° C. Roxadustat (2 g) was added to the resultant mixture at 65° C. and stirred for 20-30 minutes. The resultant mixture was filtered under vacuum. Filtered solution was added to the other crystallization vessel at 65° C. The reaction mixture was cooled to −20° C. and stirred for 2-3 hours. The obtained material was filtered and dried in Vacuum Tray Dryer (VTD) at 45° C. for 2-3 hours to obtain the title co-crystal.

Example-14: Preparation of Co-Crystal of Roxadustat with Nicotinamide (Form RNM)

Methanol (7 mL) was dispensed into a crystallization vessel at room temperature and it was heated to 45° C. Nicotinamide (0.694 g) was added to hot methanol. To the above mixture acetone (70 mL) was added at 45° C. Roxadustat (2 g) was added to the resultant solution at 45° C. and stirred for 20-30 minutes. The resultant mixture was filtered under vacuum at 45° C. Filtered solution was added to the other crystallization vessel at 45° C. The reaction mixture was cooled to −20° C. and stirred for 2-3 hours. The obtained material was filtered and dried in Vacuum Tray Dryer (VTD) at 45° C. for 2-3 hours to obtain the title co-crystal.

Example-15: Preparation of Co-Crystal of Roxadustat with Urea (Form RU)

Ethanol (4 m L) was dispensed into a crystallization vessel at room temperature and it was heated to 45° C. Urea (0.693 g) was added to hot ethanol. To the above mixture Acetone (20 mL) was added at 45° C. Roxadustat (1 g) was added to the resultant dispersion at 45° C. and stirred for 5-10 minutes. The resultant mixture was filtered under vacuum. Filtrate was left under suction drying at RT for 22 hours to obtain the title co-crystal.

Example-16: Preparation of Crystalline Roxadustat Form-γ

Roxadustat (25 g) was dissolved in formic acid (112.5 mL) at about 60° C. The solution was filtered at room temperature for particle free. The obtained clear solution was charged into reactor and cooled 0-5° C. and seeded the reaction mass with Roxadustat delta form to make slurry and maintained for about 1 hour. Water (1013 mL) was slowly added to the slurry for about 1 hour and maintained for 1 hour. The reaction mass temperature was raised 25-30° C. and maintained for 2-3 hours. The obtained solid was filtered under vacuum, washed with water (30 mL) and dried in VTD at about 40° C. for 2 hours to obtain the title compound. Yield: 92%

Example-17: Preparation of Co-Crystal of Roxadustat with L-Proline

Roxadustat (35 g) was dissolved in a mixture of methanol, acetone and water (117 mL/1165.5 mL/58.1 mL) at about 45-50° C. and the solution was filtered for particle free. L-proline (11.44 g) was dissolved separately in water (58.1 mL) and filtered for particle free. Charged the clear L-proline solution into the above solution slowly for about 5-10 minutes at about 45-50° C. The reaction mass was cooled to 0-5° C. for about 60 minutes and maintained for 15-18 hours. The obtained solid was filtered under vacuum and washed with DM-water (20 mL) and dried in VTD at about 40° C. for 2 hours to obtain the title compound.

Yield: 58%

We claim:

1. A crystalline Roxadustat Form-δ, characterized by X-ray powder diffraction pattern having peaks at about 6.57, 9.21, 18.10, 19.67, 20.86, 25.10 and 29.47±0.2° 2θ.

2. The crystalline form according to claim 1, Roxadustat Form-δ as defined in claim 1, characterized by X-ray powder diffraction pattern having additional peaks at about 13.02, 13.84 and 22.78+0.2° 2θ.

3. A process for preparation of crystalline Roxadustat Form-δ as defined in claim 1, comprising;
   a) slurrying crystalline Roxadustat form-γ in water;
   b) optionally, heating the solution of step a);
   c) isolating the crystalline Roxadustat Form-δ;
   d) optionally, drying the product.

4. A process for preparation of crystalline Roxadustat Form-δ as defined in claim 2, comprising;
   a) slurrying crystalline Roxadustat form-γ in ater;
   b) optionally, heating the solution of step a);
   c) isolating the crystalline Roxadustat Form-δ;
   d) optionally, drying the product.

* * * * *